US008001975B2

(12) United States Patent
DiSilvestro et al.

(10) Patent No.: US 8,001,975 B2
(45) Date of Patent: Aug. 23, 2011

(54) MEDICAL DEVICE COMMUNICATIONS NETWORK

(75) Inventors: Mark R. DiSilvestro, Columbia City, IN (US); Jason T. Sherman, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 1416 days.

(21) Appl. No.: 11/024,905

(22) Filed: Dec. 29, 2004

(65) Prior Publication Data
US 2006/0140139 A1 Jun. 29, 2006

(51) Int. Cl.
*A61B 19/00* (2006.01)
(52) U.S. Cl. ...................................... 128/899
(58) Field of Classification Search ................ 128/899; 600/37, 463, 485, 486, 365, 510; 607/23, 607/60, 9; 370/310, 252; 340/7.3, 309.4; 700/214, 232, 236
See application file for complete search history.

(56) References Cited

U.S. PATENT DOCUMENTS

| 5,193,539 | A | 3/1993 | Schulman et al. |
| 5,197,488 | A | 3/1993 | Kovacevic |
| 5,360,016 | A | 11/1994 | Kovacevic |
| 5,425,775 | A | 6/1995 | Kovacevic et al. |
| 5,469,862 | A | 11/1995 | Kovacevic |
| 5,523,746 | A | 6/1996 | Gallagher |
| 5,545,191 | A | 8/1996 | Mann et al. |
| 5,626,630 | A | 5/1997 | Markowitz et al. |
| 5,833,603 | A | 11/1998 | Kovacs et al. |
| 5,861,019 | A | 1/1999 | Sun et al. |
| 5,967,986 | A | 10/1999 | Cimochowski et al. |
| 6,034,296 | A | 3/2000 | Elvin et al. |
| 6,115,636 | A | 9/2000 | Ryan |
| 6,169,925 | B1 | 1/2001 | Villaseca et al. |
| 6,324,418 | B1 | 11/2001 | Crowley et al. |
| 6,385,593 | B2 * | 5/2002 | Linberg .......................... 705/28 |
| 6,447,448 | B1 | 9/2002 | Ishikawa et al. |
| 6,456,256 | B1 | 9/2002 | Amundson et al. |

(Continued)

FOREIGN PATENT DOCUMENTS

EP 1264614 A2 5/2002

(Continued)

OTHER PUBLICATIONS

National Semiconductor LM62 2.7V, 15.6 mV/°C, SOT-23 Temperature Sensor, Jun. 1999 (7 pages) 2001 National Semiconductor Corporation Article.

(Continued)

*Primary Examiner* — Charles A Marmor, II
*Assistant Examiner* — Christine D Hopkins
(74) *Attorney, Agent, or Firm* — Barnes & Thornburg LLP

(57) ABSTRACT

A medical device communications network comprises a plurality of medical devices including either or both of a first number of surgical instruments and a second number of implants configured for subcutaneous implantation in a biological body. A corresponding plurality of wireless communication circuits are each mounted to a different one of the plurality of medical devices. Each of the plurality of wireless communication circuits is configured to broadcast medical device information relating to the medical device to which it is mounted and to receive information relating to any other of the plurality of medical devices. The network may or may not include a master wireless communications circuit configured to receive the medical device information broadcast by any of the plurality of slave wireless communication circuits and to broadcast the information relating to any other of the plurality of medical devices.

2 Claims, 3 Drawing Sheets

U.S. PATENT DOCUMENTS

| | | |
|---|---|---|
| 6,539,947 B2 * | 4/2003 | Boies et al. ............... 128/899 |
| 6,577,901 B2 | 6/2003 | Thompson |
| 6,628,989 B1 | 9/2003 | Penner et al. |
| 6,631,296 B1 | 10/2003 | Parramon et al. |
| 6,656,117 B2 | 12/2003 | Jentsch et al. |
| 6,706,005 B2 | 3/2004 | Roy et al. |
| 6,708,065 B2 | 3/2004 | Von Arx et al. |
| 6,802,811 B1 | 10/2004 | Slepian |
| 7,047,076 B1 | 5/2006 | Li et al. |
| 7,256,695 B2 | 8/2007 | Hamel et al. |
| 2002/0013613 A1 | 1/2002 | Haller et al. |
| 2002/0013614 A1 | 1/2002 | Thompson |
| 2002/0024450 A1 | 2/2002 | Townsend et al. |
| 2002/0040234 A1 | 4/2002 | Linberg |
| 2002/0082665 A1 | 6/2002 | Haller et al. |
| 2002/0091310 A1 | 7/2002 | Jentsch et al. |
| 2002/0177782 A1 | 11/2002 | Penner |
| 2002/0177884 A1 | 11/2002 | Ahn et al. |
| 2002/0183806 A1 | 12/2002 | Abrahamson et al. |
| 2003/0069644 A1 | 4/2003 | Kovacevic et al. |
| 2003/0093503 A1 | 5/2003 | Yamaki et al. |
| 2003/0172940 A1 | 9/2003 | Rogers et al. |
| 2004/0010184 A1 | 1/2004 | Kenknight et al. |
| 2004/0011366 A1 | 1/2004 | Schulman et al. |
| 2004/0019382 A1 | 1/2004 | Amirouche et al. |
| 2004/0049245 A1 | 3/2004 | Gass et al. |
| 2004/0073279 A1 | 4/2004 | Malackowski |
| 2004/0078219 A1 | 4/2004 | Kaylor et al. |
| 2004/0113790 A1 | 6/2004 | Hamel et al. |
| 2004/0204744 A1 | 10/2004 | Penner et al. |
| 2005/0010299 A1 | 1/2005 | Disilvestro |
| 2005/0010301 A1 | 1/2005 | Disilvestro et al. |
| 2005/0010302 A1 | 1/2005 | Dietz et al. |
| 2005/0061336 A1 * | 3/2005 | Goetz et al. ............... 128/899 |

FOREIGN PATENT DOCUMENTS

| | | |
|---|---|---|
| WO | 92/17113 A1 | 10/1992 |
| WO | 00/13585 A1 | 3/2000 |
| WO | 0119239 A1 | 3/2001 |
| WO | 0143823 A1 | 6/2001 |
| WO | WO 01/48675 | 7/2001 |
| WO | 03066159 A2 | 8/2003 |
| WO | 03095024 A2 | 11/2003 |
| WO | WO 2004/028627 | 4/2004 |
| WO | WO 2004/030757 | 4/2004 |
| WO | WO 2004/030759 | 4/2004 |
| WO | 2004/039256 A2 | 5/2004 |

OTHER PUBLICATIONS

Surgeon at Scripps Clinic Implants One-of-a-Kind "Electronic Knee"—Revolutionizing Research in Knee Implant Technology (3 pages) Scripps Clinic Oct. 21, 2004 Article.

"Application Note" nRF24E1 and nRF24E2 Rf layout nAN24-03 Jun. 2004 (6 pages) Nordic Semiconductor ASA (Revision 2.0).

European Search Report for EP Application No. 052577612-2305, Mar. 13, 2006, 3 pages.

* cited by examiner

MEDICAL DEVICE COMMUNICATIONS NETWORK

FIELD OF THE INVENTION

The present invention relates generally to systems for conducting wireless communications, and more specifically to such systems for communicating information relating to medical devices such as surgical instruments, medical implant devices, computer assisted surgery devices, and the like.

BACKGROUND

During the lifetime of a patient, it may be desirable to perform one or more surgical procedures on the patent as a result of, for example, disease or trauma. A number of medical implants, surgical instruments and computer assisted surgery devices may be utilized during the performance of such a procedure.

SUMMARY

The present invention may comprise one or more of the features recited in the attached claims, and/or one or more of the following features and combinations thereof. A medical device communications network may comprise a plurality of medical devices including either or both of a first number of surgical instruments and a second number of implants configured for subcutaneous implantation in a living biological body, and a corresponding plurality of wireless communication circuits each mounted to a different one of the plurality of medical devices. Each of the plurality of wireless communication circuits may be configured to broadcast medical device information, wherein the medical device information relates to the medical device to which it is mounted, and to receive information relating to any other of the plurality of medical devices. At least one of the first number of surgical instruments may be controlled by a computer aided surgery device.

Each of the plurality of wireless communications circuits may include a visual indicator. Each of the plurality of wireless communications circuits may control operation of its corresponding visual indicator based on the information relating to any other of the plurality of medical devices. Each of the plurality of wireless communication circuits may be operable to activate its corresponding visual indicator if the medical device to which it is mounted is incompatible with any other of the plurality of medical devices. Alternatively or additionally, each of the plurality of wireless communication circuits may be operable to activate its corresponding visual indicator if the medical device to which it is mounted is being used out of order relative to an established medical device usage sequence.

Alternatively or additionally, each of the plurality of wireless communications circuits may include an audible indicator. Each of the plurality of wireless communications circuits may control operation of its corresponding audible indicator based on the information relating to any other of the plurality of medical devices. Each of the plurality of wireless communication circuits may be operable to activate its corresponding audible indicator if the medical device to which it is mounted is incompatible with any other of the plurality of medical devices. Alternatively or additionally, each of the plurality of wireless communication circuits may be operable to activate its corresponding audible indicator if the medical device to which it is mounted is being used out of order relative to an established medical device usage sequence.

In one embodiment, the network does not include a master communications device and instead information relating to any other of the plurality of medical devices includes the medical device information broadcast by any other of the plurality of medical devices.

In another embodiment, each of the plurality of wireless communication circuits may be a slave wireless communication circuit. The network in this embodiment may further include a master wireless communication circuit configured to receive the medical device information broadcast by any of the plurality of slave wireless communication circuits and to broadcast the information relating to any other of the plurality of medical devices. Each of the slave wireless communication circuits may include a visual or audible indicator operable as described above. Alternatively or additionally, the master wireless communications circuit may include a visual indicator. The master wireless communications circuit may control operation of the visual indicator based on the information broadcast by any of the plurality of slave wireless communication circuits. The master wireless communication circuit may be operable to activate the visual indicator if any of the plurality of medical devices are incompatible with each other. Alternatively or additionally, the master wireless communication circuit may be operable to activate the visual indicator if any of the plurality of medical devices are used out of order relative to an established medical device usage sequence. Alternatively or additionally, the master wireless communications circuit may include an audible indicator. The master wireless communications circuit may control operation of the audible indicator based on the information broadcast by any of the plurality of slave communication circuits. The master wireless communication circuit may be operable to activate the audible indicator if any of the plurality of medical devices are incompatible with each other. Alternatively or additionally, the master wireless communication circuits may be operable to activate the audible indicator if any of the plurality of medical devices are used out of order relative to an established medical device usage sequence.

An additional wireless communication circuit may be introduced into the network. The additional wireless communication network may be configured to become the master communication circuit when introduced into the network. If the network includes an existing master wireless communication circuit, the existing master wireless communication circuit may then become another of the slave wireless communication circuits.

These and other features of the present invention will become more apparent from the following description of the illustrative embodiments.

DESCRIPTION OF THE ILLUSTRATIVE EMBODIMENTS

Figure 1:
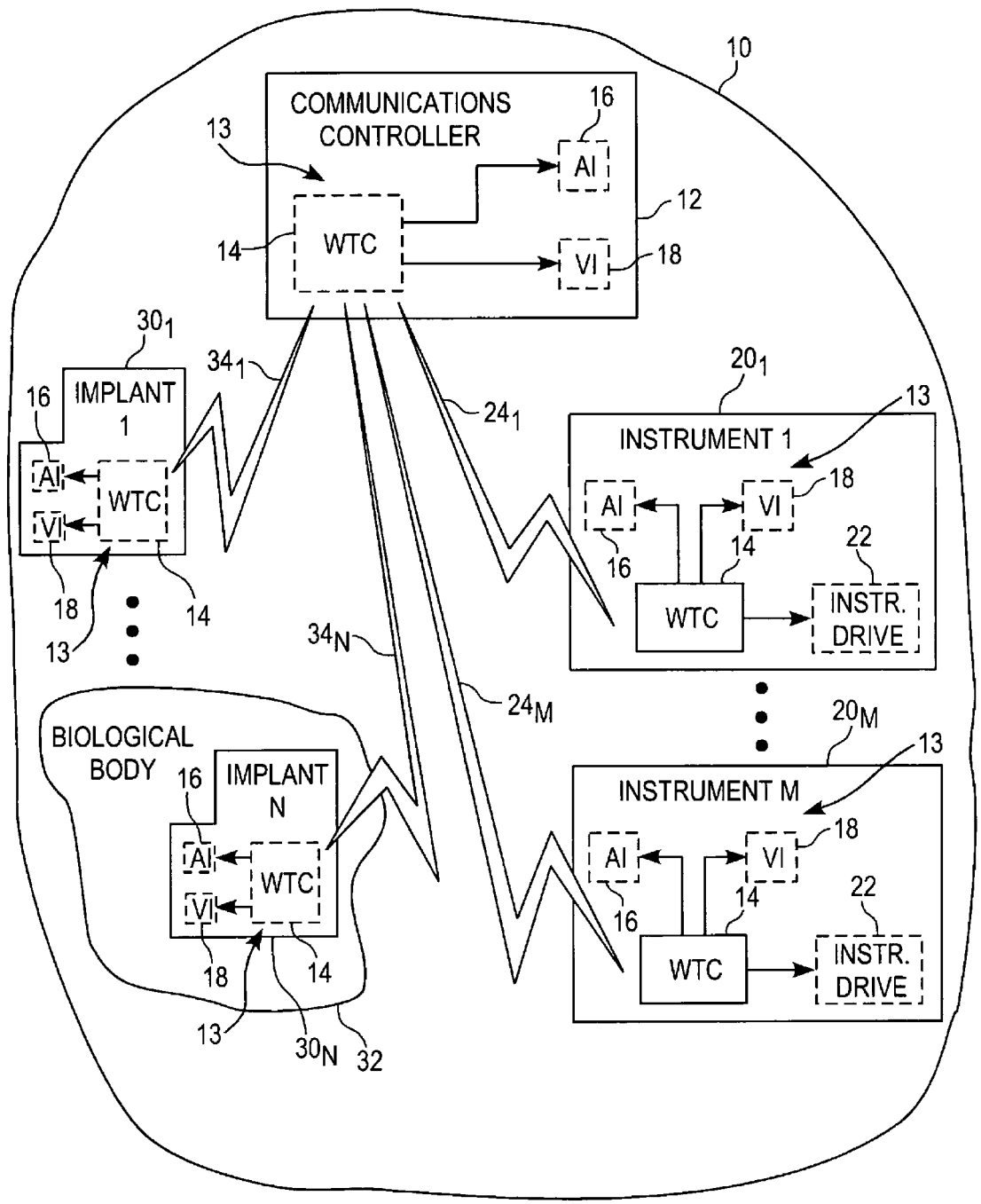
FIG. 1 is a diagram of one illustrative embodiment of a medical device communications network.

For the purposes of promoting an understanding of the principles of the invention, reference will now be made to a number of illustrative embodiments illustrated in the drawings and specific language will be used to describe the same.

Referring now to FIG. 1, a diagrammatic illustration of one illustrative embodiment of a wireless network environment 10 is shown in the context of a portion of an operating room or other space for performing surgical procedures. In the illustrated embodiment, the wireless network environment 10 includes a communications controller 12, a number, M, of surgical instruments $20_1$-$20_M$, and a number, N, of medical implants $30_1$-$30_N$, wherein M and N may each be any positive integer. The communications controller 12 includes a wireless communications circuit 13 having a wireless transceiver circuit 14 electrically connected to either one, or both of, an audible indicator 16 and a visual indicator 18. The audible indicator 16 may be any conventional electronically actuatable audible device responsive to an electrical activation signal to emit a natural or synthesized audible sound. Examples of conventional devices that may be used as the audible indicator 16 include, but are not limited to, a bell, a buzzer, a chime, or any other audible device configured to produce a single one, series or sequence of sounds in response to the activation signal. The visual indicator 18 may likewise be any conventional device responsive to an electrical activation signal to emit, produce or display a visible event. Examples of conventional devices that may be used as the visual indicator 18 include, but are not limited to, one or more lamps, light emitting diodes (LEDs), vacuum fluorescent, liquid crystal or other types of displays, monitors or the like.

Each of the number, M, of medical instruments $20_1$-$20_M$ includes a wireless communications circuit 13 having a wireless transceiver circuit 14 which may be electrically connected to either one, or both of, an audible indicator 16 and a visual indicator 18, wherein the devices 14, 16 and 18 may be as described hereinabove. Additionally, the wireless transceiver circuit 14 may be electrically coupled or connected to an instrument drive mechanism 22 configured to control one or more functional operations of the medical instrument. The wireless transceiver circuits 14 carried by each of the number, M, of medical instruments $20_1$-$20_M$ are configured to share information with the wireless transceiver circuit 14 of the communications controller 12 via corresponding wireless communication paths $24_1$-$24_M$. Any one or more of the medical instruments $20_1$-$20_M$ may be controlled by a computer aided surgery device (not shown).

The number N of medical implants $30_1$-$30_N$ also have mounted thereto a wireless communication circuit 13 having a wireless transceiver circuit 14 which may be electrically connected to either one, or both of, an audible indicator 16 and a visual indicator 18, wherein the devices 14, 16 and 18 may be as described hereinabove. At any time during a surgical procedure, any one or more of the medical implants $30_1$-$30_N$ may be resident within a living biological body 32, as shown by example for the medical implant $30_N$ or may instead be external to the biological body 32 as shown by example with the medical implant $30_1$. In any case, the wireless transceiver circuits 14 of the medical implant $30_1$-$30_N$ are configured to share information with the wireless transceiver circuit 14 of the communications controller 12 via corresponding wireless communication paths $34_1$-$34_N$. In the embodiment illustrated in FIG. 1, the communications controller 12 operates as a "master" or "hub" device and is accordingly operable in a conventional manner to receive all communications from any one or more of the medical instruments $20_1$-$20_M$ and any one or more of the medical implants $30_1$-$30_N$, and to selectively transmit information back to any one or more of the medical instruments $20_1$-$20_M$ and/or medical implants $30_1$-$30_N$. The communications controller 12 continuously performs device discovery by monitoring information broadcast by any one or more of the medical instruments $20_1$-$20_M$ and any one or more of the medical implants $30_1$-$30_N$. In this configuration, each of the medical instruments $20_1$-$20_M$ and medical implants $30_1$-$30_N$ are configured to continually broadcast a device identification code (device ID) unique to that device, and the communications controller 12 is accordingly operable to continually determine and monitor the presence of all medical instruments $20_1$-$20_M$ and medical implants $30_1$-$30_N$ that are within the wireless communications network environment 10.

Examples of information that may be transmitted from any one or more of the medical instruments $20_1$-$20_M$ include, but are not limited to medical instrument model, type and/or ID as well as any functional information relating to the operability, operating state and/or operating conditions of the medical instrument. Examples of such medical instrument functionality include, but are not limited to, battery charge, estimated battery charge remaining, ON/OFF state of the medical instrument, operating speed of the medical instrument, or the like. Examples of information that may be transmitted to the wireless communication module 14 of the communications controller 12 from any one or more of the medical implants $30_1$-$30_N$ include, but are not limited to implant model, type, ID, and the like.

The communications controller 12 is generally operable to monitor the types and sequences of the medical instruments $20_1$-$20_M$ and medical implants $30_1$-$30_N$ used in a medical procedure to ensure that appropriate instruments are matched with appropriate devices, and that the medical procedure being performed is carried out according to a predefined sequence of steps and/or that the medical instruments $20_1$-$20_M$ and/or medical implants $30_1$-$30_N$ are used in a predefined sequence. The communications controller 12 is configured to provide an audible or visual warning to the user, via any one or more of the audible indicators 16 and/or visual indicators 18 associated with the communication controller 12 and/or appropriate ones of the medical instruments $20_1$-$20_M$ and/or medical implants $30_1$-$30_N$, in any of a number of scenarios. One example scenario may occur when, by processing information broadcast by the various medical instruments $20_1$-$20_M$ and medical implants $30_1$-$30_N$, the communications controller 12 determines that one or more of the medical instruments $20_1$-$20_M$ and/or medical implants $30_1$-$30_N$ is/are incompatible with any one or more other ones of the medical instruments $20_1$-$20_M$ and/or medical implants $30_1$-$30_N$. Another example scenario may occur when, by processing information broadcast by the various medical instruments $20_1$-$20_M$ and medical implants $30_1$-$30_N$, the communications controller 12 determines that one of the medical instruments $20_1$-$20_M$ and/or medical implants $30_1$-$30_N$ is being used in an incorrect order, according to a specified medical device usage sequence or surgical technique, relative to the other ones of the medical instruments $20_1$-$20_M$ and/or medical implants $30_1$-$30_N$. Other example scenarios will occur to those skilled in the art, and any such scenarios are contemplated by the present disclosure.

Figure 2:
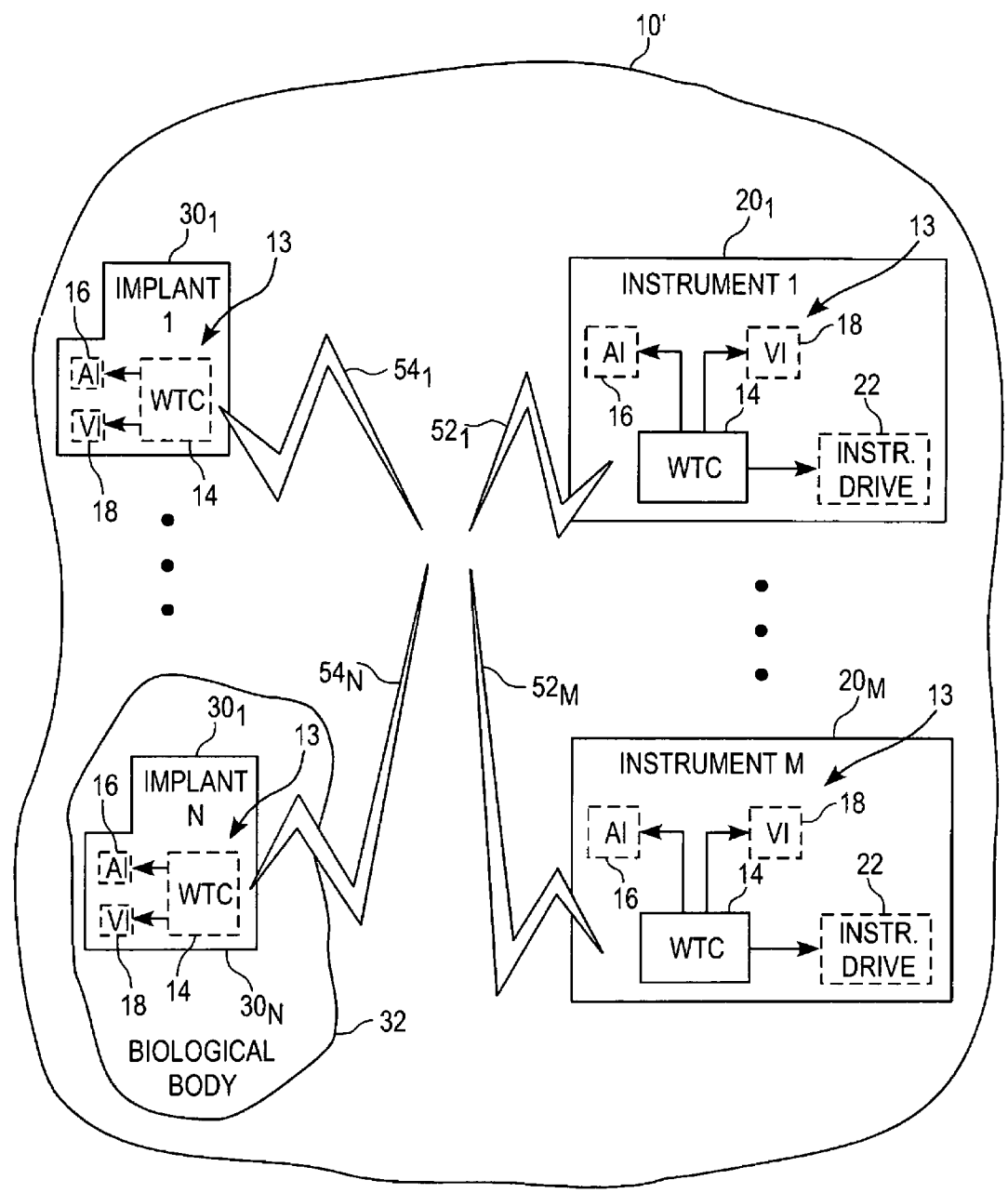
FIG. 2 is a diagram of another illustrative embodiment of medical device communications network

Referring now to FIG. 2, a diagrammatic illustration of another illustrative embodiment of a wireless network environment 10' is shown in the context of a portion of an operating room or other space for performing surgical procedures. In the illustrated embodiment, the wireless network environment 10' includes a number, M, of surgical instruments $20_1$-$20_M$, and a number, N, of medical implants $30_1$-$30_N$, wherein M and N may each be any positive integer.

Each of the number, M, of medical instruments $20_1$-$20_M$ includes a wireless communications circuit 13 having a wireless transceiver circuit 14 which may be electrically connected to either one, or both of, an audible indicator 16 and a visual indicator 18, wherein the devices 14, 16 and 18 may be as described hereinabove. Additionally, the wireless transceiver circuit 14 may be electrically coupled or connected to an instrument drive mechanism 22 configured to control one or more functional operations of the medical instrument. The wireless transceiver circuits 14 carried by each of the number, M, of medical instruments $20_1$-$20_M$ are configured to broadcast and receive information via corresponding wireless communication paths $52_1$-$52_M$. Any one or more of the medical instruments $20_1$-$20_M$ may be controlled by a computer aided surgery device (not shown).

The number N of medical implants $30_1$-$30_N$ also have mounted thereto a wireless communication circuit 13 having a wireless transceiver circuit 14 which may be electrically connected to either one, or both of, an audible indicator 16 and a visual indicator 18, wherein the devices 14, 16 and 18 may be as described hereinabove. At any time during a surgical procedure, any one or more of the medical implants $30_1$-$30_N$ may be resident within a living biological body 32, as shown by example for the medical implant $30_N$ or may instead be external to the biological body 32 as shown by example with the medical implant $30_1$. In any case, the wireless transceiver circuits 14 of the medical implant $30_1$-$30_N$ are configured to broadcast and receive information via corresponding wireless communication paths $54_1$-$54_N$.

In the embodiment illustrated in FIG. 2, the wireless network environment 10' does not include a master or hub device, and instead each of the medical instruments $20_1$-$20_M$ are configured to receive information broadcast by any one or more of the medical implants $30_1$-$30_N$, and vice versa. In this configuration, each of the medical instruments $20_1$-$20_M$ and medical implants $30_1$-$30_N$ is configured to continually broadcast a device identification code (device ID) unique to that device, and all others of the medical instruments $20_1$-$20_M$ and medical implants $30_1$-$30_N$ within the wireless network environment 10' are configured to receive the broadcast ID information. Examples of information that may be transmitted from any one or more of the medical instruments $20_1$-$20_M$ and medical implants $30_1$-$20_N$ include, but are not limited to medical instrument model, type and/or ID.

The wireless network illustrated in FIG. 2 is generally operable to monitor the types and sequences of the medical instruments $20_1$-$20_M$ and medical implants $30_1$-$30_N$ used in a medical procedure to ensure that appropriate instruments are matched with appropriate devices, and that the medical procedure being performed is carried out according to a predefined sequence of steps and/or that the medical instruments $20_1$-$20_M$ and/or medical implants $30_1$-$30_N$ are used in a predefined sequence. Each of the wireless communication circuits 13 is configured to broadcast information relating to the medical instrument $20_1$-$20_M$ or medical implant $30_1$-$30_N$ to which it is mounted, and to receive information relating to any other of the medical instrument $20_1$-$20_M$ or medical implant $30_1$-$30_N$. Each of the wireless communication circuits 13 carried by the various medical instruments $20_1$-$20_M$ and medical implants $30_1$-$30_N$ is configured to provide an audible or visual warning to the user, via a corresponding audible indicator 16 and/or visual indicators 18, in any of a number of scenarios. One example scenario may occur when the wireless communication circuit 13 of any one or more of the medical instruments $20_1$-$20_M$ and/or medical implants $30_1$-$30_N$ determines that the associated medical instrument $20_1$-$20_M$ or medical implant $30_1$-$30_N$ is incompatible with any one or more other ones of the medical instruments $20_1$-$20_M$ and/or medical implants $30_1$-$30_N$. Another example scenario may occur when the wireless communication circuit 13 of any one or more of the medical instruments $20_1$-$20_M$ and/or medical implants $30_1$-$30_N$ determines that one of the medical instruments $20_1$-$20_M$ and/or medical implants $30_1$-$30_N$ is being used in an incorrect order, according to a specified medical device usage sequence or surgical technique, relative to the other ones of the medical instruments $20_1$-$20_M$ and/or medical implants $30_1$-$30_N$. Other example scenarios will occur to those skilled in the art, and any such scenarios are contemplated by the present disclosure.

Figure 3:
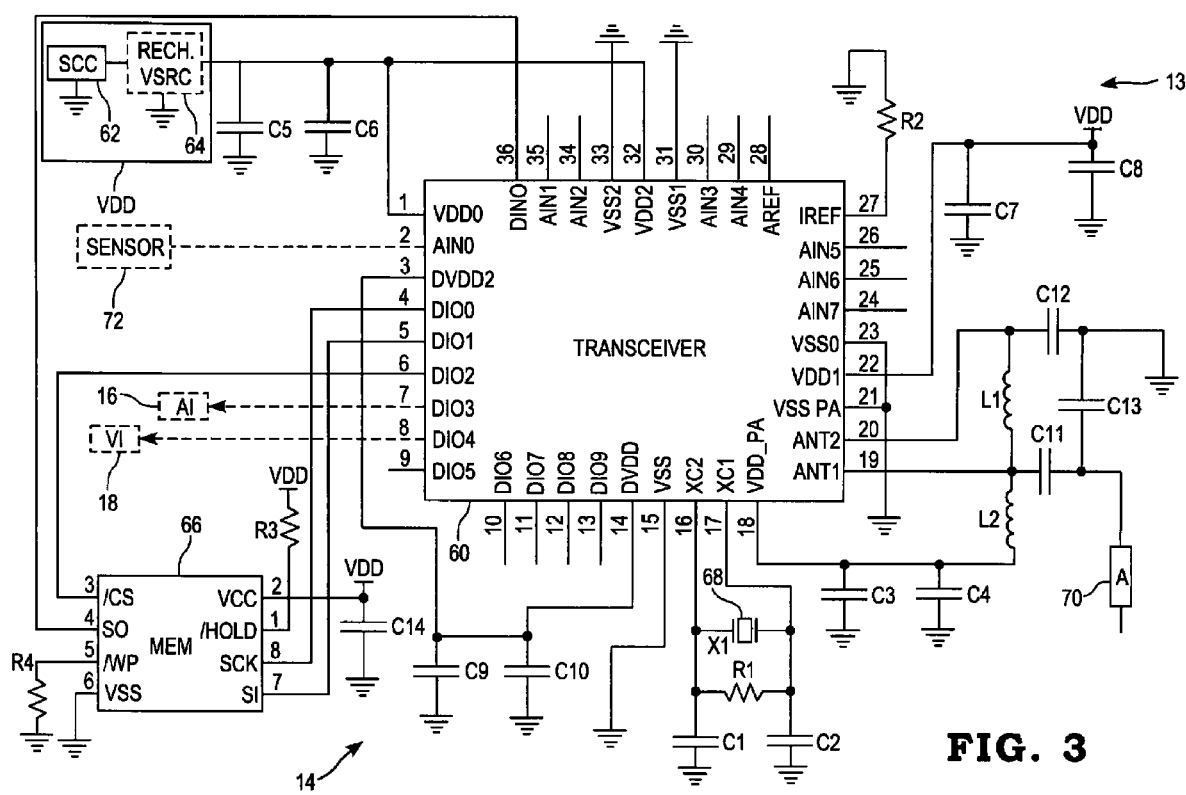
FIG. 3 is a schematic diagram of one illustrative embodiment of a wireless communication circuit carried by the one or more medical devices of the network of either of FIG. 1 or 2.

Referring now to FIG. 3, a schematic diagram of one illustrative embodiment of the wireless communications circuit 13 of FIGS. 1 and 2 is shown. Central to the wireless communication circuit 13 is a wireless transceiver circuit 14 including a transceiver circuit 60 operable to broadcast information using conventional wireless communications technology. The transceiver circuit 60 may be, for example, an nRF241E1, 2.4 GHz RF transceiver/transmitter that is commercially available through Nordic Semi-Conductor ASA of Tiller, Norway, although the present disclosure contemplates that the transceiver circuit 60 may alternatively be any known transceiver circuit capable of broadcasting information in the radio frequency range (e.g., 402-405 MHz or so-called MICS band) or other frequency range including, but not limited to, sub radio frequencies, or other conventional protocols including, but not limited to, Bluetooth©, ZigBee©, Wi-Fi, Wireless USB, and the like. The transceiver circuit 60 operates at a supply voltage, VDD, and at a clock frequency generated by a conventional crystal 68. The crystal 68 in the illustrated embodiment is a 16 MHz crystal, although crystals operating at other clock frequencies may be used.

The wireless transceiver circuit 14 further includes a voltage source supplying the operating voltage VDD. In one embodiment, for example, the voltage source may be provided in the form of a conventional secondary coil circuit 62 configured to inductively couple to a conventional primary coil circuit. In this embodiment, the secondary coil circuit includes a conventional secondary inductive coil that is electrically connected to a conventional AC-to-DC conversion circuit. When an energized primary coil (not shown) inductively couples with the secondary coil, an AC voltage is induced in the secondary coil according to known physical principles. The induced AC voltage is converted to the supply voltage, VDD, by the AC-to-DC conversion circuit. This DC voltage may be supplied directly to the VDD supply line (e.g., VDD0 and VSS2), or may alternatively be provided to a rechargeable voltage source 64 interposed between the secondary coil circuit 62 and the operating voltage supply line as shown in phantom in FIG. 3. In the former case, the wireless transceiver circuit 14 has no internal voltage source, and may be activated for operation only when the secondary coil circuit 14 is inductively coupled to an activated primary coil circuit. Such a supply voltage arrangement will typically be implemented with the wireless communication circuits 13 mounted to any one or more of the medical implants $30_1$-$30_N$. In the latter case, the rechargeable voltage source 64 is operable to produce the operating voltage, VDD, for some time period between recharging events. When this embodiment is implemented in any of the wireless communication circuits 13 mounted to any one or more of the medical implants $30_1$-$30_N$, however, the secondary coil circuit 62 must be periodically coupled to an activated primary coil circuit so that the secondary coil circuit 62 produces the DC supply voltage, VDD, for a sufficient time to recharge the rechargeable voltage source 64. The wireless communication circuit 13 mounted to any of the medical instruments $20_1$-$20_M$ and/or carried by the communications controller 12, need not include the secondary coil circuit 62, and may instead include only a conventional rechargeable or non-rechargeable voltage source supplying the supply voltage, VDD. The wireless communication circuits 13 mounted to the various medical instruments $20_1$-$20_M$ and medical implants $30_1$-$30_N$ are, in one embodiment, configured to be mounted to the devices in a manner that allows for repeated attachment and detachment of the circuits 13 from their respective devices to facilitate cleaning, sterilization, etc. of the various medical instruments $20_1$-$20_M$ and medical implants $30_1$-$30_N$. This feature further allows the circuits 13 to be removed from their respective medical implants $30_1$-$30_N$, if desired, after implantation thereof.

In the embodiment illustrated in FIG. 3 wherein the transceiver circuit 60 is a nRF241E1, 2.4 GHz RF transceiver/transmitter produced by Nordic Semi-Conductor, such a transceiver circuit does not include sufficient memory for storage of program code and/or any generated data. Accordingly, a separate memory circuit 66 is provided for the purpose of storing one or more executable algorithms and/or storing data. In the illustrative embodiment, the memory circuit 66 is a 4.0 Kbyte serial EEPROM that is commercially available through any number of semiconductor manufacturers. In other embodiments, the transceiver circuit 60 may include sufficient on-board memory, in which case the memory circuit 66 may be omitted.

In the illustrated embodiment, the wireless transceiver circuit 14 is configured for short-range wireless communication, and in this regard a single-ended antenna 70 is connected via a differential-to-single ended matching network, comprising L1, L2, C3-C4 and C11-C13 to differential antenna inputs, ANT1 and ANT2, of the transceiver circuit 60. In the illustrated embodiment, the antenna 70 is a 50 OHM antenna that may be implemented in any variety of known antenna configurations.

The wireless communication circuit 13 may include one or more sensors producing sensor signals indicative of one or more corresponding operating conditions of the medical device with which the wireless communication circuit 13 is associated. For example, the wireless communication circuit 13 may be mounted to a medical implant, as illustrated in FIGS. 1 and 2, that is then subsequently implanted into living biological tissue. In this case, one or more sensors may be suitably positioned relative to the medical implant to provide one or more corresponding sensor signals indicative of one or more corresponding operating characteristics of the implant. Examples of such operating characteristics may include, but are not limited to, temperature, load, strain, torque and the like. As another example, the wireless communication circuit 13 may be mounted to a surgical instrument as illustrated in FIGS. 1 and 2. In this case, one or more sensors may be suitably positioned relative to the surgical instrument to provide one or more corresponding sensor signals indicative of one or more corresponding operating parameters of the surgical instrument. Alternatively or additionally, the surgical instrument may be part of a computer assisted surgery device, and may in such cases be controlled by the computer assisted surgery device. In such cases, one or more sensors may be suitably positioned relative to the surgical instrument and/or one or more of the computer assisted surgery components to provide one or more corresponding sensor signals indicative of one or more corresponding operating parameters of the computer assisted surgery device. In either case, examples of such operating parameters may include, but are not limited to, instrument (e.g., saw, drill, etc.) speed, implement position, implement operating direction, instrument operating temperature, and the like. In the embodiment illustrated in FIG. 3, the wireless communication circuit 13 may include a general operating condition sensor 72 as shown in phantom, which may be or include any sensor of the foregoing type that is electrically connected to one of the analog inputs, e.g., AIN0, of the transceiver circuit 60. Sensory data produced by the sensor 72 may be routed by the transceiver circuit 60 to the memory circuit 66 for storage therein and subsequent wireless transmission via the antenna 70 within the wireless communication network illustrated in either of FIGS. 1 and 2. Alternatively, the transceiver circuit 60 may be operable to transmit the sensory data in real time via the antenna 70 in a conventional manner.

The wireless communication circuit 13 may further include either one or both of an audible indicator 16 and a visual indicator 18 of the types described hereinabove. In the illustrated embodiment, for example, an audible indicator 16 may be electrically connected to a digital or analog output (e.g., DI03) of the transceiver circuit 60 and the visual indicator 18 may also be electrically connected to a digital or analog output (e.g., DI04) of the transceiver circuit 60. The transceiver circuit 60 is operable to control operation of the audible indicator 16 and/or visual indicator 18, as described hereinabove, in a conventional manner.

The remaining electrical components illustrated in FIG. 3 are provided to support operation of the transceiver circuit 60 and memory circuit 66. Typical values of the illustrated components for one specific implementation of the wireless communication circuit 13 are provided in the following Table 1. In this specific implementation of the wireless communication circuit 13, the rechargeable voltage source 64 is not included, and the operating condition sensor 72 is implemented as a single temperature sensor. It will be understood that such component values are provided only way of example, and that other component values may be used.

TABLE 1

| Component Identification | Description | Physical Size | Value | Tolerance | Units |
|---|---|---|---|---|---|
| C1 | Ceramic Capacitor, 50 V, NPO | 0603/0402 | 22 | ±5% | pF |
| C2 | Ceramic Capacitor, 50 V, NPO | 0603/0402 | 22 | ±5% | pF |
| C3 | Ceramic Capacitor, 50 V, NPO | 0603/0402 | 22 | ±5% | pF |
| C4 | Ceramic Capacitor, 50 V, X7R | 0603/0402 | 2.2 | ±10% | nF |
| C5 | Ceramic Capacitor, 50 V, X7R | 0603/0402 | 1.0 | ±10% | nF |
| C6 | Ceramic Capacitor, 50 V, X7R | 0603/0402 | 10 | ±10% | nF |
| C7 | Ceramic Capacitor, 50 V, X7R | 0603/0402 | 10 | ±10% | nF |
| C8 | Ceramic Capacitor, 50 V, X7R | 0603/0402 | 1.0 | ±10% | nF |
| C9 | Ceramic Capacitor, 50 V, X7R | 0603/0402 | 1.0 | ±10% | nF |
| C10 | Ceramic Capacitor, 50 V, X7R | 0603/0402 | 33 | ±10% | nF |
| C11 | Ceramic Capacitor, 50 V, NPO | 0603/0402 | 1.0 | ±0.25 pF | pF |
| C12 | Ceramic Capacitor, 50 V, NPO | 0603/0402 | 1.0 | ±0.25 pF | pF |
| C13 | Ceramic Capacitor, 50 V, NPO | 0603/0402 | 1.5 | ±0.25 pF | pF |

TABLE 1-continued

| Component Identification | Description | Physical Size | Value | Tolerance | Units |
|---|---|---|---|---|---|
| C14 | Ceramic Capacitor, 50 V, X7R | 0603/0402 | 10 | ±10% | nF |
| L1 | Inductor, wire wound | 0603/0402 | 3.6 | ±5% | nH |
| L2 | Inductor, wire wound | 0603/0402 | 22 | ±5% | nH |
| R1 | Resistor | 0603/0402 | 1.0 | ±1% | Mohm |
| R2 | Resistor | 0603/0402 | 22 | ±1% | Kohm |
| R3 | Resistor | 0603/0402 | 10 | ±1% | Kohm |
| R4 | Resistor | 0603/0402 | 10 | ±1% | Kohm |
| 60 | nRF241E1 (Nordic VLSI) | QFN36/6 × 6 | | | |
| 66 | 4 Kbyte serial EEPROM with SPI interface | SO8 | 2XX320 | | |
| 68 | Crystal, $C_L$ = 12 pF, ESR < 100 ohm | L × W × H = 4.0 × 2.5 × 0.8 | 16 | +/−30 ppm | MHz |
| 72 | LM62 2.7 V, 15.6 mV/° C. Temperature Sensor (National Semiconductor) | SOT-23 | | | |

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected. For example, the present disclosure contemplates that either of the networks illustrated and described with respect to FIGS. 1 and 2 may be configured in a known manner to recognize the introduction of a "superior" master device, such as another controller or computer assisted surgery (CAS) device into the network field or environment 10 or 10'. In such cases, the "superior" master device will assume control over the communications in the same manner as described hereinabove with respect to the communications controller 12. In networks that have a communications controller 12, the superior master device will assume control and the controller 12 will be relegated to the status of a slave wireless communication circuit similar to the wireless communication circuits 13 mounted to the various medical devices 20₁-20_M and 30₁-30_N. This feature allows a newly introduced wireless communication device or controller with one or more superior or desirable features to assume control of the communications environment. Examples of some such superior or desirable features include, but are not limited to, superior data processing power, longer battery life, or other desirable metric.

What is claimed is:

1. A medical device communications network comprising:
   a plurality of medical devices including a first number of surgical instruments and a second number of implants configured for subcutaneous implantation in a living biological body,
   a corresponding plurality of slave wireless communication circuits each mounted to a different one of the plurality of medical devices, each of the plurality of slave wireless communication circuits configured to broadcast medical device information relating to the medical device to which it is mounted, and to receive information relating to any other of the plurality of medical devices,
   a master wireless communication circuit configured to receive the medical device information broadcast by any of the plurality of slave wireless communication circuits and to broadcast the information relating to any other of the plurality of medical devices,
   an additional wireless communication circuit to be introduced into the network, the additional wireless communication circuit configured to become the master communication circuit when introduced into the network with the existing master wireless communication circuit then becoming another of the slave wireless communication circuits.

2. A medical device communications network comprising:
   a plurality of medical devices,
   a corresponding plurality of slave wireless communication circuits each mounted to a different one of the plurality of medical devices, each of the plurality of slave wireless communication circuit configured to broadcast information relating to the medical device to which it is mounted and to receive information relating to any other of the plurality of medical devices,
   a master wireless communication circuit configured to receive the information broadcast by any of the plurality of slave wireless communication circuits and to broadcast the information relating to any other of the plurality of medical devices, and
   an additional wireless communication circuit to be introduced into the network, the additional wireless communication circuit configured to become the master communication circuit when introduced into the network with the existing master wireless communication circuit then becoming another of the slave wireless communication circuits.

* * * * *